United States Patent
Dambacher et al.

(10) Patent No.: US 9,629,750 B2
(45) Date of Patent: Apr. 25, 2017

(54) SURGICAL LASER UNIT WITH VARIABLE MODES OF OPERATION

(75) Inventors: Florian Dambacher, Haag (DE); Markus Hailmann, Sachsenhausen (DE); Frieder Loesel, Mannheim (DE); Gwillem Mosedale, Munich (DE)

(73) Assignee: TECHNOLAS PERFECT VISION GMBH, Munich (DE)

( * ) Notice: Subject to any disclaimer, the term of this patent is extended or adjusted under 35 U.S.C. 154(b) by 0 days.

(21) Appl. No.: 13/450,180

(22) Filed: Apr. 18, 2012

(65) Prior Publication Data
US 2013/0281991 A1 Oct. 24, 2013

(51) Int. Cl.
*A61F 9/008* (2006.01)
*A61F 9/009* (2006.01)

(52) U.S. Cl.
CPC .......... *A61F 9/00825* (2013.01); *A61F 9/009* (2013.01); *A61F 2009/00897* (2013.01)

(58) Field of Classification Search
CPC .......... A61F 9/008; A61F 9/013; A61F 9/009; A61F 2009/00825; A61F 2009/00897
USPC ........................................................ 606/4
See application file for complete search history.

(56) References Cited

U.S. PATENT DOCUMENTS

| | | |
|---|---|---|
| 3,169,459 A | 2/1965 | Friedberg |
| 4,169,664 A | 10/1979 | Bailey, Jr. |
| 4,573,778 A | 3/1986 | Shapiro |
| 4,846,172 A | 7/1989 | Berlin |
| 4,881,808 A | 11/1989 | Bille |
| 4,891,043 A | 1/1990 | Zeimer et al. |
| 4,907,586 A | 3/1990 | Bille et al. |
| 4,995,715 A | 2/1991 | Cohen |
| 5,098,426 A | 3/1992 | Sklar et al. |
| 5,246,435 A | 9/1993 | Bille |

(Continued)

FOREIGN PATENT DOCUMENTS

| | | |
|---|---|---|
| EP | 0765648 A2 | 4/1997 |
| EP | 0798987 B1 | 2/2001 |

(Continued)

OTHER PUBLICATIONS

Sacks et al., High Precision Subsurface Photodisruption in Human Sclera, Journal of Biomedical Optics, Jul. 2002, pp. 442-450, vol. 7, No. 3.

(Continued)

*Primary Examiner* — Gary Jackson
*Assistant Examiner* — Boniface N Nganga
(74) *Attorney, Agent, or Firm* — Nydegger & Associates

(57) ABSTRACT

A comprehensive multi-mode system for performing ophthalmic laser surgery on selected tissue inside an eye includes a laser unit for generating and focusing a laser beam to perform Laser Induced Optical Breakdown (LIOB) at a focal point in selected tissue. Also included is a selector for defining an operational mode according to characteristics of the tissue to be altered by LIOB. In combination, the operational mode specifies value ranges for configuration parameters for a pulsed femtosecond laser beam, establishes a base reference datum in the eye, and identifies a scanning procedure for the focal point of the laser beam to customize the system for a particular surgical procedure. A computer that is connected to the laser unit is responsive to the selector for implementing the operational mode.

13 Claims, 3 Drawing Sheets

(56) References Cited

U.S. PATENT DOCUMENTS

| | | |
|---|---|---|
| 5,439,462 A | 8/1995 | Bille |
| 5,480,396 A | 1/1996 | Simon et al. |
| 5,720,894 A | 2/1998 | Neev et al. |
| 5,779,696 A | 7/1998 | Berry et al. |
| 5,984,916 A | 11/1999 | Lai |
| 5,993,438 A | 11/1999 | Juhasz et al. |
| 6,004,314 A | 12/1999 | Wei et al. |
| 6,010,497 A | 1/2000 | Tang et al. |
| 6,059,772 A | 5/2000 | Hsia et al. |
| 6,099,522 A | 8/2000 | Knopp et al. |
| 6,322,556 B1 | 11/2001 | Gwon et al. |
| 6,391,020 B1 | 5/2002 | Kurtz et al. |
| 6,454,761 B1 | 9/2002 | Freedman |
| 6,467,906 B1 | 10/2002 | Alpins |
| 6,485,413 B1 | 11/2002 | Boppart et al. |
| 6,514,241 B1 | 2/2003 | Hsia et al. |
| 6,579,282 B2 | 6/2003 | Bille |
| 6,966,905 B2 | 11/2005 | Bille |
| 7,027,233 B2 | 4/2006 | Goldstein et al. |
| 7,232,436 B2 | 6/2007 | Bille |
| 7,458,380 B2 | 12/2008 | Jones et al. |
| 7,618,415 B2 | 11/2009 | Kessler et al. |
| 7,655,002 B2 | 2/2010 | Myers |
| 7,699,467 B2 | 4/2010 | Dick et al. |
| 7,703,923 B2 | 4/2010 | Bille |
| 7,731,362 B2 | 6/2010 | Gerlach |
| 7,789,910 B2 | 9/2010 | Knox et al. |
| 7,800,760 B2 | 9/2010 | Bille |
| 7,950,398 B2 | 5/2011 | Schroeder et al. |
| 8,088,124 B2 | 1/2012 | Loesel et al. |
| 8,231,221 B2 | 7/2012 | Donitzky et al. |
| 2002/0173778 A1 | 11/2002 | Knopp et al. |
| 2002/0198516 A1 | 12/2002 | Knopp et al. |
| 2003/0074150 A1 | 4/2003 | Goldstein et al. |
| 2004/0199149 A1 | 10/2004 | Myers et al. |
| 2005/0165387 A1 | 7/2005 | Lubatschowski et al. |
| 2005/0192562 A1* | 9/2005 | Loesel et al. ............ 606/5 |
| 2006/0195076 A1 | 8/2006 | Blumenkranz et al. |
| 2008/0009922 A1 | 1/2008 | Bille |
| 2008/0025351 A1* | 1/2008 | Loesel ............ 372/25 |
| 2008/0177256 A1* | 7/2008 | Loesel et al. ............ 606/4 |
| 2008/0281303 A1 | 11/2008 | Culbertson et al. |
| 2009/0069794 A1 | 3/2009 | Kurtz |
| 2009/0137993 A1 | 5/2009 | Kurtz |
| 2009/0143772 A1 | 6/2009 | Kurtz |
| 2009/0149841 A1 | 6/2009 | Kurtz |
| 2010/0004643 A1 | 1/2010 | Frey et al. |
| 2010/0022994 A1* | 1/2010 | Frey et al. ............ 606/4 |
| 2010/0022995 A1* | 1/2010 | Frey et al. ............ 606/4 |
| 2010/0022996 A1* | 1/2010 | Frey et al. ............ 606/6 |
| 2010/0076417 A1 | 3/2010 | Suckewer et al. |
| 2010/0082017 A1 | 4/2010 | Zickler et al. |
| 2010/0114079 A1 | 5/2010 | Myers et al. |
| 2010/0191230 A1 | 7/2010 | Dick et al. |
| 2010/0290007 A1 | 11/2010 | Van de Velde |
| 2010/0324542 A1 | 12/2010 | Kurtz |
| 2010/0324543 A1* | 12/2010 | Kurtz et al. ............ 606/6 |
| 2011/0040293 A1 | 2/2011 | Bor |
| 2011/0040376 A1 | 2/2011 | Christie et al. |
| 2011/0118712 A1 | 5/2011 | Lubatschowski et al. |
| 2011/0144628 A1 | 6/2011 | Vogler |
| 2011/0160710 A1 | 6/2011 | Frey et al. |
| 2011/0166557 A1 | 7/2011 | Naranjo-Tackman et al. |
| 2011/0190741 A1 | 8/2011 | Deisinger et al. |
| 2011/0202044 A1 | 8/2011 | Goldshleger et al. |
| 2011/0202046 A1 | 8/2011 | Angeley et al. |
| 2011/0319875 A1 | 12/2011 | Loesel et al. |
| 2012/0078240 A1* | 3/2012 | Spooner ............ 606/5 |
| 2012/0078241 A1* | 3/2012 | Gooding ............ A61F 9/009 606/6 |
| 2012/0150160 A1 | 6/2012 | Vogler et al. |
| 2012/0172854 A1 | 7/2012 | Raymond et al. |

FOREIGN PATENT DOCUMENTS

| | | |
|---|---|---|
| EP | 1252872 A1 | 2/2002 |
| WO | WO2008112292 A1 | 9/2008 |
| WO | WO2010076799 A3 | 7/2010 |
| WO | 2010129916 A2 | 11/2010 |
| WO | WO 2011011202 A1 * | 1/2011 |
| WO | 2012038011 A1 | 3/2012 |
| WO | WO2013053367 A1 * | 4/2013 |

OTHER PUBLICATIONS

Chai et al., Aqueous Humor Outflow Effects of Partial Thickness Channel Created by a Femtosecond Laser in Ex Vivo Human Eyes, Optical Interactions with Tissue and Cells XVIII, 2007, pp. 1-8, Proc of SPIE, vol. 6435.

PCT International Search Report, Application No. PCT/IB2013/000681, Apr. 15, 2013.

* cited by examiner

SURGICAL LASER UNIT WITH VARIABLE MODES OF OPERATION

FIELD OF THE INVENTION

The present invention pertains generally to laser systems for performing ophthalmic laser surgeries. More particularly, the present invention pertains to laser systems that can be customized to perform a particular surgical laser procedure on a specifically identified ophthalmic tissue. The present invention is particularly, but not exclusively, useful as a system and method for customizing a same laser system to selectively perform different ophthalmic surgeries by specifying a laser beam configuration, establishing a base reference datum for the system, and identifying a scanning mode for each particular surgical procedure.

BACKGROUND OF THE INVENTION

Any ophthalmic laser surgical procedure requires a combination of precision, accuracy and efficacy that must be maintained within the range of the operational capabilities of the laser system that is being used. Thus, the system itself, or a particular subcomponent of the system, can be a limiting factor for a surgical procedure. Moreover, there are many different operational requirements, and many different operational factors that are unique for each ophthalmic laser procedure. Stated differently, the surgical requirements for a laser system will change depending on the particular procedure that is to be followed and on the specific part of the eye where the surgery is to be performed. A consequence of all this is the need for a versatile laser system.

With recent improvements in so-called "femtosecond" laser systems, as well as in imaging techniques such as Optical Coherence Tomography (OCT), it is now possible to perform laser surgical procedures deep into the eye. No longer is the cornea the only ophthalmic tissue of interest for laser surgery. Specifically, laser surgical procedures involving the crystalline lens, trabecular meshwork, sclera, vitreous and retina are now being considered for laser surgery. Not surprisingly, each of these different tissues in the eye has its own unique set of operational and anatomical issues.

As is well known, the Laser Induced Optical Breakdown (LIOB) of ophthalmic tissue can be efficaciously employed using a pulsed femtosecond laser beam in many different surgical procedures. Alternative tissue interactions with the related effects may use nanosecond or picosecond laser pulses. These procedures include LASIK flap, corneal surgery (e.g. Keretoplasty), refractive corrections, cataract related surgeries, tissue relaxing incisions, glaucoma surgery, and posterior/retinal surgeries. As implied above, each case for LIOB is unique and each procedure has its own particular requirements. Consequently, although similar considerations for the employment of LIOB may be required in each of these different cases/procedures, they will inevitably lead to different operational conclusions. Primarily, the required considerations include: reference datum, laser patient interface, laser beam configuration, focal point placement, and focal point scanning. Importantly, these considerations are interrelated and must be evaluated in the context of other considerations.

With the above in mind, the specification for a Maser beam configuration involves the selection of value ranges for operational parameters that will best accomplish the required alteration of a selected target tissue. In particular, based on the specific anatomical features that will be involved, the selection of operational parameters typically includes: 1) choosing an appropriate wavelength for the laser beam; 2) determining "fluence" (energy density) at specific locations along the beam path; 3) selecting a pulse energy; 4) establishing a pulse rate; 5) setting a pulse duration; 6) selecting an appropriate patient interface; and 7) setting a focusing means.

Insofar as the focal point placement is concerned, in addition to the anatomical considerations for the type of tissue that is being targeted, it may also be necessary to consider the proximity of the target tissue to a different type of tissue (i.e. the location of a tissue interface). In the event, within permissible cost restraints, the placement of a focal point will preferably be accomplished with the greatest possible precision. In all cases this means that an appropriate, cost effective, base reference datum needs to be established. And, the focal point of the laser beam must be accurately located relative to the base reference datum. For ophthalmic surgeries, such a base reference datum may be a point, a line (e.g. an axis), or a surface. Further, the precision required for establishing the reference datum may need to involve the use of high-level mathematical computations (e.g. expansion series), and/or sophisticated imaging techniques such as OCT.

In addition to laser beam configuration and focal point placement, all ophthalmic laser surgeries require the selection of an appropriate scanning operation. Specifically, this selection will generally involve the identification of a focal point path, along with the determinations of the rate of focal point movements and the spacing between adjacent focal points. This may also involve calibration requirements for the entire laser beam generating unit.

As an additional consideration for customizing an appropriate laser system for performing an ophthalmic surgery, it is necessary to evaluate the particular patient interface that is to be used. In particular, any distortions of the eye that may be caused when stabilizing the eye with a patient interface (i.e. a contact lens) needs to be accounted for. In some instances the possible adverse effects may be minimal and, therefore, generally acceptable. On the other hand, such distortions may degrade optical qualities of the laser beam to the point where the laser beam becomes ineffective. Suffice to say, the patient interface may be a critical factor for consideration with creating an efficacious surgical laser system.

In light of the above, it is an object of the present invention to provide a system and method for performing ophthalmic laser surgery on selected tissue in an eye which allows for customizing the system based on considerations of the specific requirements of a particular surgical procedure. Another object of the present invention is to provide a system and method for performing an ophthalmic laser surgical procedure with a specific patient interface, which allows a user to selectively specify a laser beam configuration, in combination with a selectively established base reference datum, and a selectively identified scanning mode. Yet another object of the present invention is to provide a system and method for performing an ophthalmic laser surgical procedure which is easy to use, is simple to establish and is cost effective.

SUMMARY OF THE INVENTION

In accordance with the present invention, a multi-mode operable laser system can be customized to perform ophthalmic laser surgery on selected tissue inside an eye. Structurally, the system includes a laser unit, for generating a laser beam, and for focusing the laser beam to a focal point.

Preferably, the laser beam is a pulsed femtosecond laser beam that can be configured to perform a Laser Induced Optical Breakdown (LIOB) procedure on the selected target tissue.

A mode selector is operationally connected with the laser unit to establish and define an operational mode for the system. This is, done by selecting system functionalities, based on compatibility considerations, that are best suited to perform the required surgical procedure on the selected target tissue. In detail, the operational mode includes:

1) a specification of the configuration parameters that are to be used for the laser beam, to include the wavelength of the laser beam, fluence measurements along the laser beam, pulse power, pulse rate and pulse duration;

2) a process for establishing a base reference datum in the eye that uses point selection, axis selection, expansion series and/or real-time imaging or detector techniques; and 3) a plan for moving the focal point of the laser beam in accordance with a defined scanning procedure, wherein the scanning procedure is based on considerations of the rate of focal spot movement, spacing between focal points, pattern description (e.g. raster or spiral) and calibration points.

In addition to the laser unit and the mode selector, the system of the present invention also includes a computer for controlling the laser unit. More specifically, the computer is connected to both the laser unit and to the mode selector. With these connections, the computer is responsive to the mode selector to control the laser unit for the purpose of implementing the operational mode.

An additional feature of the system involves considerations for the incorporation of a patient interface. Whenever such an interface is used, its purpose is to stabilize a patient's eye during ophthalmic surgery. It can happen, however, that the use of an interface can introduce optical distortions into the eye. As a practical consideration, patient interfaces can have different levels of effect, on different areas of the eye, depending on whether they are a planar contact lens, a curved contact lens, a conformable (e.g. water filled) contact lens, or contact free. In the event, they may affect other functional aspects of a customized laser system and, therefore, they must be considered and accounted for in the system set-up and subsequent operations.

Due to the plethora of set-up possibilities for different operational modes, and due to the distinct possibility that one particular operational mode may be satisfactory for a a sequence of surgical procedures on respectively different patients, the present invention provides for a so-called default operational mode. Accordingly, the functionalities that constitute the operational mode are preselected. In detail, the configuration parameters for the laser beam are preset, the process for establishing the base reference datum is preset, and the plan for scanning the laser beam's focal point is also preset. Flexibility for the system, however, is provided by allowing the system user to move from the default status of any functionality, as desired.

With the above disclosure in mind, it is to be appreciated that the present invention envisions an operation of the system which includes switching between two different operational modes. For example, consider an integrated operation that requires both a cataract surgery and corneal incisions. In such an integrated operation, the particular procedure that will be deeper in the eye (i.e. the cataract surgery) will likely be done first. In any event, the set-up for both modes of operation can be accomplished prior to starting the integrated operation.

In line with earlier disclosure, each procedure (cataract surgery and corneal incisions) will be accomplished separately, and may require different operational modes. In this case, the system set-up initially requires that compatibility considerations be made for an operational mode to perform cataract surgery (i.e. a first operational mode). This involves determining the appropriate operational parameters for the laser beam (e.g. fluence and spot size), establishing a base reference datum, prescribing scanning patterns, and employing a patient interface (e.g. pressure on the eye) for a cataract surgery (e.g. capsulotomy and lens fragmentation).

Following the establishment of the first mode of operation (e.g. cataract surgery) a second mode of operation (e.g. corneal incisions) is established by essentially repeating the same compatibility considerations made for the first mode. This requires additional evaluations and appropriate adjustments of the laser beam's operational parameters and scanning patterns, possibly the selection of a new base reference datum, and a possible modulation of the patient interface. More specifically, insofar as the patient interface is concerned, it can likely happen that only very little pressure needs to be exerted on the eye during the cataract surgery portion of the integrated operation. This minimal pressure is generally preferable in order to minimize posterior and other corneal deformations that could otherwise introduce unwanted distortions of the laser beam. On the other hand, greater pressures are likely required during the corneal incisions portion of the integrated operation. This is so because of the need to stabilize the cornea during corneal incisions, and the fact that, in this portion of the integrated operation, posterior and other corneal deformations will have minimal effect on the procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
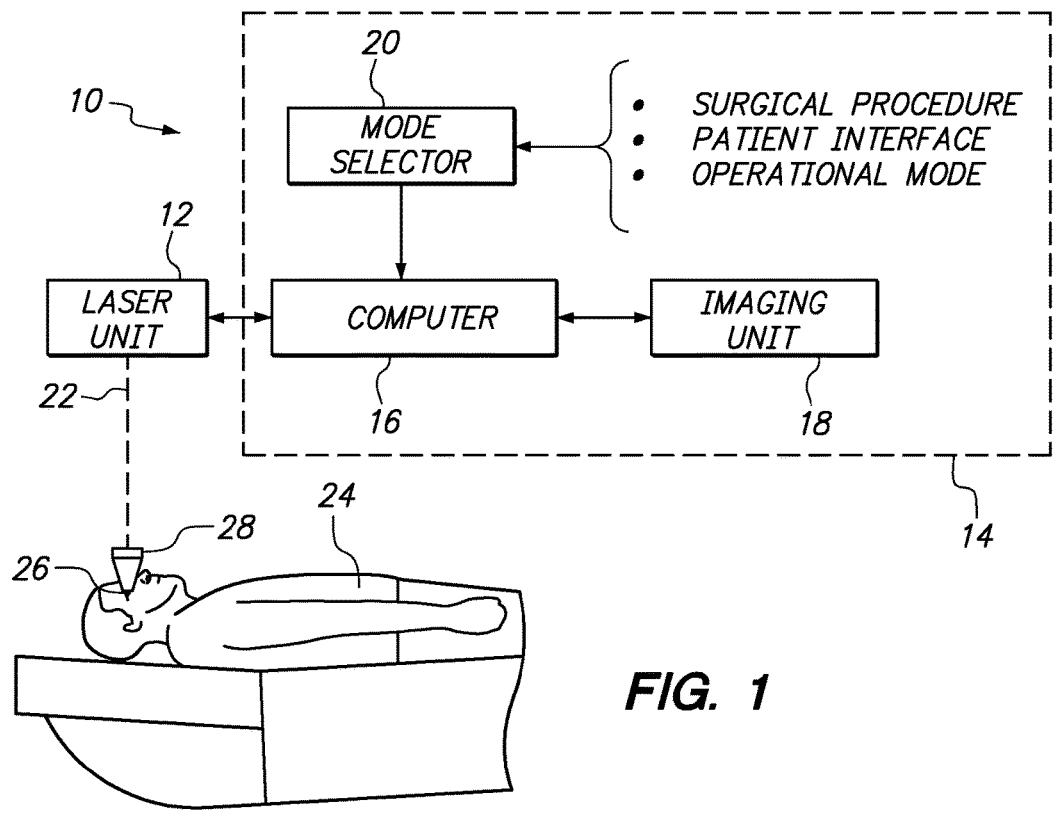
FIG. 1 is a schematic of the operational components of the present invention.

Referring initially to FIG. 1, a multi-mode system for performing ophthalmic laser surgery in accordance with the present invention is shown and is generally designated 10. As shown, the system 10 essentially includes a laser unit 12 and a control console 14. More specifically, the control console 14 includes a computer 16, an imaging (detector) unit 18 and a mode selector 20. As intended for the present invention, the control console 14 is used to first set-up and then control the operation of the laser unit 12. In particular, both set-up and control are directed to the laser beam 22 that is generated by the laser unit 12. The objective here is to effectively use the laser beam 22 to perform ophthalmic laser surgery on a patient 24, while the eye 26 is stabilized by a patient interface 28 or eye tracker (not shown).

For purposes of the present invention, the laser unit 12 will generate a so-called femtosecond laser that is capable of performing Laser Induced Optical Breakdown (LIOB) on selected tissues inside the eye 26 of the patient 24. Further, the imaging unit 18 is preferably of a type that is capable of creating three dimensional images of different tissues inside the eye 26 (e.g. an Optical Coherence Tomography (OCT) device). As envisioned for the system 10, the computer 16 will use input from the imaging unit 18 in its control of the laser unit 12 during laser ophthalmic surgeries in the eye 26.

Figure 2:
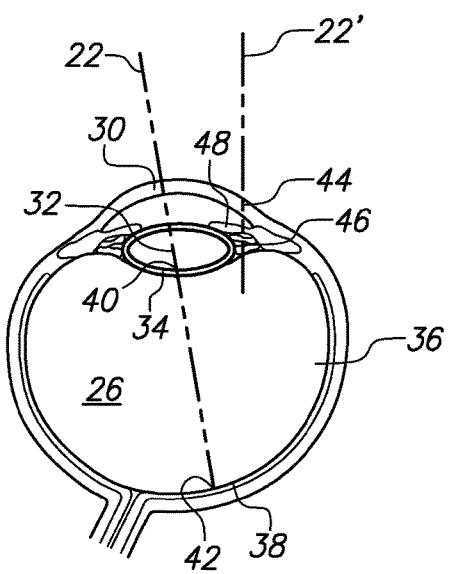
FIG. 2 is a cross section view of an eye identifying possible locations for the performance of surgical procedures envisioned for the present invention.

In FIG. 2, the extent to which ophthalmic surgeries can be performed by the system 10 inside the eye 26 will be appreciated. In particular, it will be appreciated that the system 10 envisions using a laser beam 22 to perform LIOB on tissue in the cornea 30. Further into the eye 26, it is envisioned that the system 10 can perform ophthalmic surgical procedures in/on the crystalline lens 32 and/or its capsular bag 34. Still further into the eye 26, the system 10 can be set-up and controlled to perform ophthalmic surgical procedures in the vitreous 36 of the eye 26 and in/on the retina 38. Moreover, various references for use in controlling the laser beam 22 can be established. For example, a base reference datum can be a known point in the eye 26 (not specified), a defined axis of the eye 26 (not specified), or a reference surface that is identified by the imaging unit 18. In the latter case, examples of surfaces being used for a base reference datum include the anterior surface of the cornea 30, the interface surface 40 between the crystalline lens 32 and the capsular bag 34, the posterior surface of the patient interface 28 and the interface surface 42 between the vitreous 36 and the retina 38. Furthermore, with reference to laser beam 22' in FIG. 2, it is also to be appreciated that the system 10 envisions performing LIOB surgical procedures inside the sclera 44, within the trabecular meshwork 46 and on iris tissue 48.

It will be appreciated by the skilled artisan that all tissues in the eye 26, and specifically including those tissues mentioned above, will have their own unique response to LIOB. Also, depending on the location of the particular tissue in the eye 26 (i.e. the posterior depth of the tissue in the eye 26), the laser beam 22 can be operationally affected. Moreover, the operational requirements for particular surgical procedures will differ from one procedure to another. With this in mind, it is clear there is a need to customize the system 10 in a way that will account for all operational requirements (functionalities) each time the system 10 is to be used.

Figure 3:
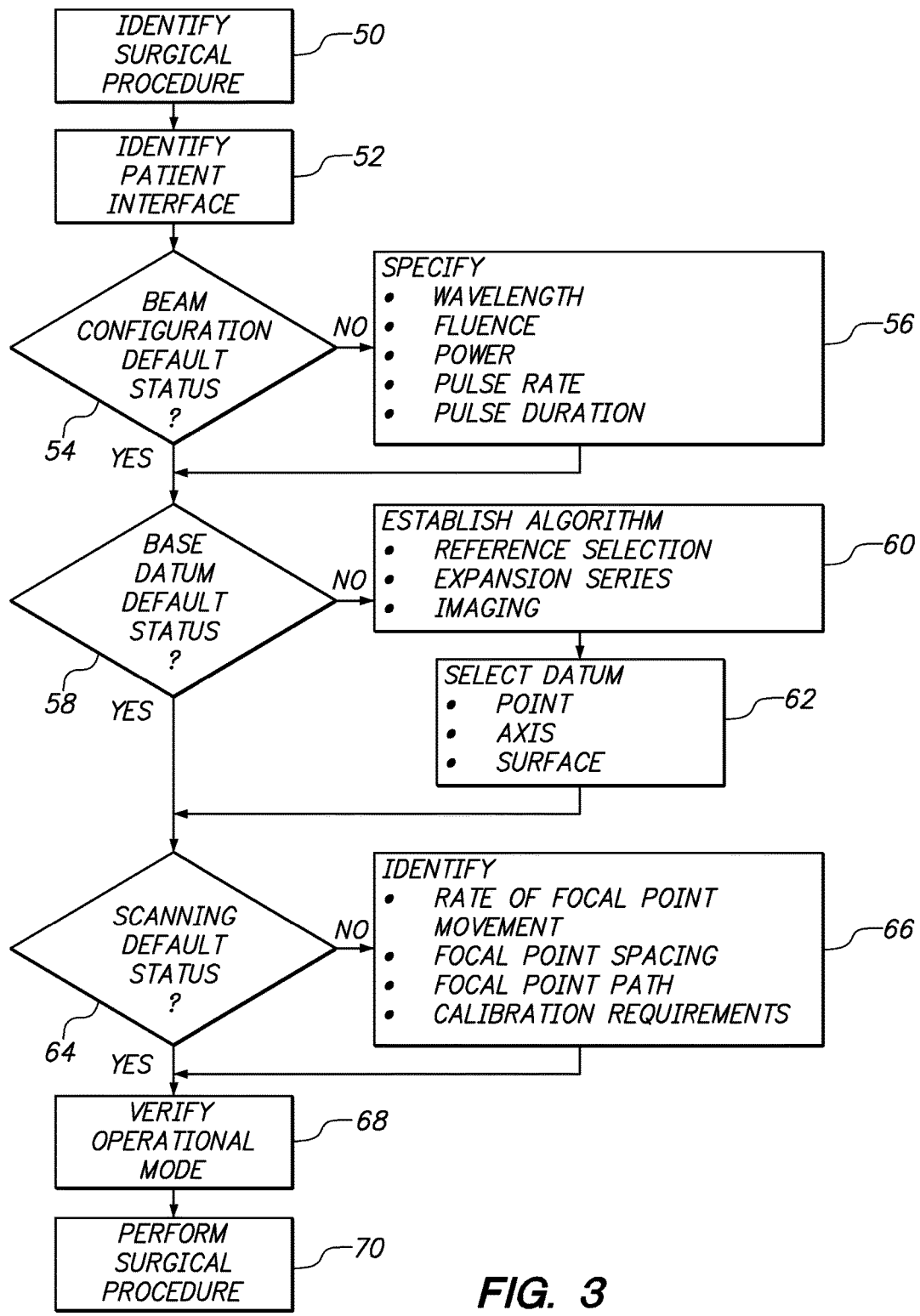
FIG. 3 is a functional flow chart showing the sequence of considerations for the various functionalities involved in a customized set-up of the laser system in accordance with present invention.

FIG. 3 is a functional flow chart that essentially presents the operational compatibility considerations which must be addressed to establish an operational mode during a set-up of the system 10. Action block 50 shows that the first consideration for the set-up is to identify the particular surgical procedure that is to be performed. As implied above, the procedure may be any of a plethora of procedures that are appropriate for a laser surgical procedure on an eye 26. Once the procedure has been identified, the next consideration is to identify the patient interface 28 that is to be used (see action block 52). As noted above, the selection of the patient interface 28 will depend on how the eye 26 can be best stabilized for the procedure, without introducing unwanted optical distortions in the laser beam 22. At this point, inquiry block 54 indicates that the system 10 will determine whether a default status is to be used for the configuration of the laser beam 22. If not, the set-up block 56 requires the user/operator to specify value ranges for configuration parameters of the laser beam 22. Specifically, these parameters will include the wavelength of the laser beam 22 and its fluence (i.e. energy density) at locations along the beam path of laser beam 22, as well as the power, pulse rate and pulse duration of the femtosecond pulses in the laser beam 22. Once the beam configuration has been determined, either by default or set-up, the next consideration concerns whether a default status is to be used for the base reference datum.

Inquiry block 58 in FIG. 3 indicates that if a default status for a base reference datum is not to be used, the user/operator is directed by set-up block 60 to establish an algorithm for such a datum. Essentially this involves selecting a technique that will provide for using a point (not specified here), an axis (not specified here), a line (not specified here), a curve (not specified here), an interface surface (not specified here), or a three dimensional surface (not specified here) as a reference datum. As is well known; this can be accomplished in any of several ways, such as by using a mathematical expansion series. Preferably, however, the present invention envisions the use of an imaging unit 18 that will employ Optical Coherence Tomography (OCT), Scheimpflug, confocal or two-photon imaging techniques. Regardless of the technique that is to be used, however, set-up block 62 requires the selection of a reference datum (e.g. a point, an axis or a surface) that can be subsequently used for control of the laser beam 22.

As a final consideration for the set-up of an operational mode for the system 10, inquiry block 64 requires identifying a particular scanning procedure for the focal point of the laser beam 22. In essence, this scanning procedure will establish a path for the focal point of laser beam 22, and define how it moves along this path. If a preset scanning procedure is not to be used as a default, set-up block 66 requires that settings be made for the rate of focal point movement, and focal point spacing on the focal point path. Additionally, calibration requirements can be attended to.

For a final check on the set up of system 10, action block 68 requires a verification of the operational mode before the particular surgical procedure is to be performed (see action block 70). As a practical matter, this verification requires confirmation as to whether the default status is to be used. If the default status is not to be used, the user/operator has the opportunity at this time to recheck and verify that the system 10 has been properly customized for the particular surgical procedure.

Figure 4:
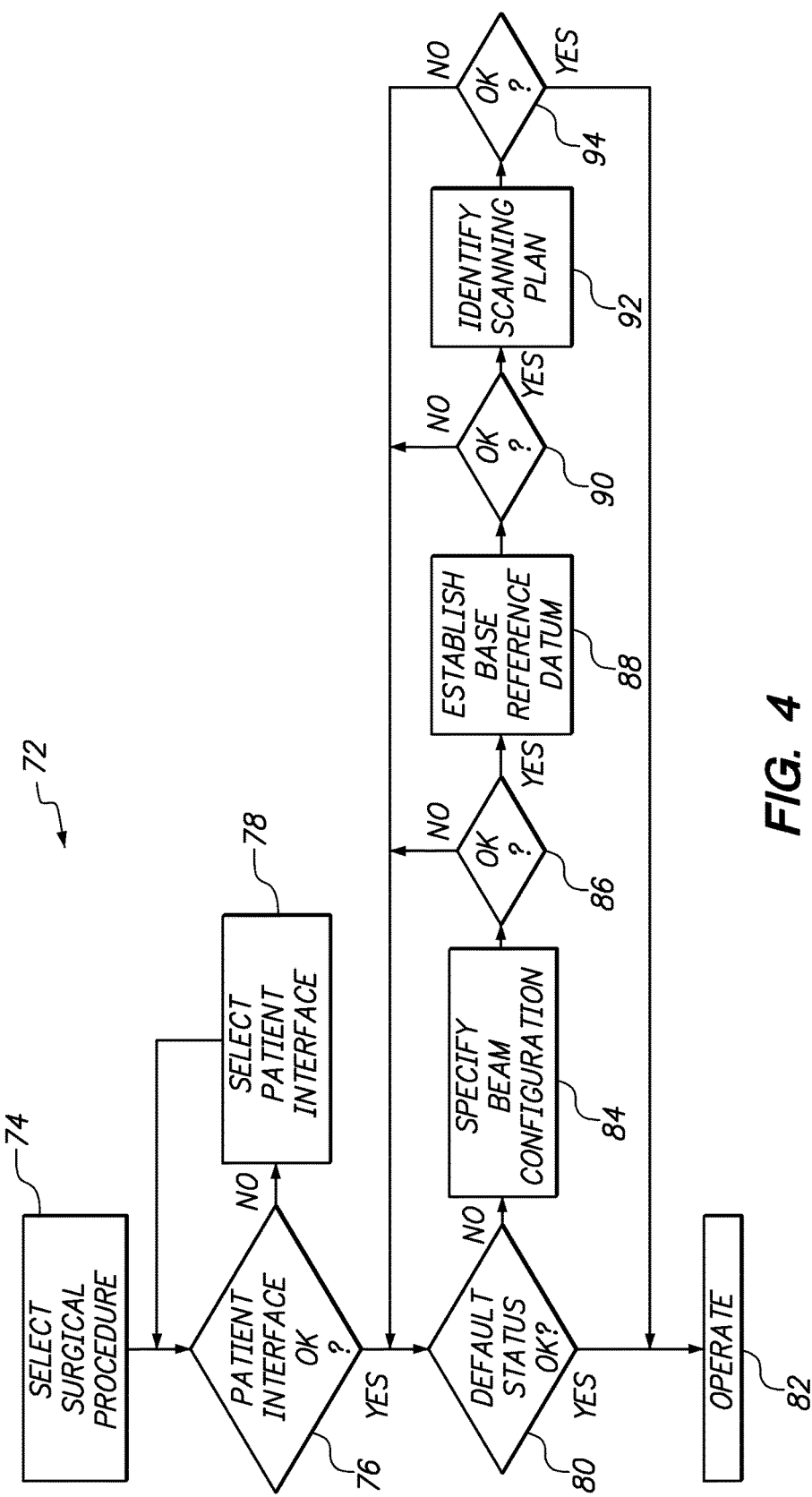
FIG. 4 is an operational flow chart to be implemented by a computer for the set-up of a laser system in accordance with the present invention.

In accordance with the present invention, the system 10 will be effectively controlled by the computer program product 16 during a surgical procedure. The computer program product 16, however, will also prompt the user/operator during the set-up of an operational mode, as has been discussed above with reference to FIG. 3. For doing this, FIG. 4 shows a simplified flow chart of the tasks that are to be accomplished by a computer program product, generally designated 72. Specifically, FIG. 4 indicates that the first requirement of the computer program product 72 is to select the surgical procedure (action block 74). Next, the computer program product 72 determines whether an appropriate patient interface 28 has been approved (inquiry block 76). If not, action block 78 requires this be done. Inquiry block 80 then determines whether a preset default status will be used for the selected surgical procedure. If so, action block 82 indicates that the surgical procedure is to be accomplished in accordance with the default operational mode that has been preset in the computer 16.

In the event a default operational mode is not to be followed by the system 10, action block 84 of the computer program 72 requires that a configuration for the laser beam 22 be specified. Once the laser beam 22 has been properly configured (inquiry block 86), the computer program 72 then requires a base reference datum be established (action block 88 and inquiry block 90). Next, a scanning plan is identified (action block 92). After all of this, inquiry block 94 then effectively determines whether an operational mode has been established for the computer program 72. If so, the computer program 72 moves to action block 82 and, thereafter, the computer 16 controls the laser unit 12 in its customized operational mode for, performance of the selected surgical procedure.

In accordance with the present invention, a computer program product 72 for performing ophthalmic laser surgery on selected tissue in an eye 26 is provided wherein the computer program product 72 comprises program sections for respectively: incorporating a laser unit 12 for generating a laser beam 22; defining an operational mode for the system 10; specifying, value ranges for configuration parameters for the laser beam 22 for implementation of the operational mode; establishing a base reference datum in the eye 26 for implementation of the operational mode; identifying a scanning procedure for the focal point of the laser beam 22 for implementation of the operational mode; and focusing the laser beam 22 to a focal point, to implement the operational mode by performing Laser Induced Optical Breakdown (LIOB) on the selected tissue. Additionally, the computer program product 72 can include program sections for: choosing a surgical procedure; and selecting a patient interface 28 from a group comprising a planar contact lens, a curved contact lens, a conformable contact lens, a fluid interface, a suction element, or air (no patient interface).

While the particular Surgical Laser Unit with Variable Modes of Operation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A multi-mode system for sequentially performing different ophthalmic laser surgeries on selected tissue in an eye which comprises:
    a laser unit for generating a pulsed laser beam, and for focusing the laser beam to a focal point, to perform a Laser Induced Optical Breakdown (LIOB) procedure on the selected tissue;
    a control console comprising a mode selector configured to prompt a user to select system functionalities relative to a default operational mode to define a first operational mode and a second operational mode for the system, wherein the first and second modes are respectively defined for LIOB of at least two different anatomical components of the eye, and wherein for each operational mode, the mode selector is configured to prompt the user to select configuration parameters for the laser beam, a process for establishing a base reference datum in the eye, a plan for scanning the focal point of the laser beam through the selected tissue relative to a selected base reference datum; a patient interface for stabilizing the eye relative to the laser unit; wherein the patient interface is established to sequentially exert a first pressure against the eye in the first operational mode and to then exert a second pressure against the eye for the second operational mode; and
    a computer connected to the laser unit and to the mode selector, wherein the computer is responsive to the mode selector for operating and switching the laser unit to selectively implement each operational mode.

2. The system as recited in claim 1 wherein the pulsed laser beam is selected from a group comprising a nanosecond, picosecond and a femtolaser source, and the configuration parameters for the laser beam are within value ranges determined by characteristics of the tissue to be altered by LIOB.

3. The system as recited in claim 2 wherein the value ranges of the configuration parameters are selected from a group that includes the wavelength of the laser beam, fluence properties along the laser beam, pulse energy, pulse rate, pulse duration, focusing of the laser beam, numerical aperture of the laser unit, and beam profile of the laser beam.

4. The system as recited in claim 1 wherein each operational mode includes a value range for pressure exerted by the patient interface against the eye, wherein a first pressure for the first operational mode is less than a second pressure for the second operational mode, and wherein the anatomical component for LIOB in the first operational mode is posterior to the anatomical component for LIOB in the second operational mode.

5. The system as recited in claim 1 wherein each base reference datum is established by a detector unit, and wherein the detector unit is selected from a group comprising an Optical Coherence Tomography (OCT), Scheimpflug, confocal imaging, optical range-finding, ultrasound, and two-photon-imaging devices.

6. The system as recited in claim 5 wherein each base reference datum is established using a technique selected from a group comprising point selection, axis selection, expansion series, interface selection, curve fitting and surface fitting.

7. The system as recited in claim 5 wherein each base reference datum is selected from a group comprising a point, an axis, a line, a curve, an interface surface, and a three dimensional surface.

8. The system as recited in claim 1 wherein each scanning plan is identified using considerations selected from a group comprising the rate of focal spot movement, focal spot spacing, pattern description and calibration points.

9. The system as recited in claim 8 wherein the patient interface is selected from a group comprising a planar contact lens, a curved contact lens, a conformable contact lens, a fluid interface and a suction element.

10. The system as recited in claim 1 wherein at least one anatomical component of the eye is selected from the group of anatomical components consisting of the cornea, the lens and the retina.

11. The system as recited in claim 1 wherein a same patient interface is used for the first operational mode and for the second operational mode.

12. A non-transitory, computer-readable medium having executable instructions stored thereon that direct a computer system to perform an ophthalmic laser surgery process on selected tissue in an eye, the instructions comprising: changing from a first operational mode to a second operational mode for the system wherein the first operational mode and the second operational mode are defined relative to a default operational mode, wherein the first and second modes are performed sequentially and are respectively defined for LOB of at least two different anatomical components of the eye, wherein the anatomical component for LOB in the first operational mode is posterior to the anatomical component for LOB in the second operational mode, with each operational mode specifying configuration parameters for a laser unit to generate a laser beam for implementation of the operational mode; establishing a base reference datum in the eye for implementation of the operational mode: establishing a first pressure against the eye in the first operational mode and a second pressure against the eye in the second operational mode, wherein the first pressure for the first operational mode is less than the second pressure for the second operational mode; identifying a scanning procedure for the focal point of the laser beam for implementation of the operational mode; and wherein the medium comprises a program section for focusing the laser beam to a focal point, to implement the selected operational mode by performing Laser Induced Optical Breakdown (LOB) on the selected tissue.

13. The medium as recited in claim 12 wherein the scanning procedure is identified for an operational mode using considerations selected from a group comprising the rate of focal spot movement and spacing, pattern description and calibration points.

\* \* \* \* \*

UNITED STATES PATENT AND TRADEMARK OFFICE
CERTIFICATE OF CORRECTION

PATENT NO.        : 9,629,750 B2                           Page 1 of 1
APPLICATION NO.   : 13/450180
DATED             : April 25, 2017
INVENTOR(S)       : Dambacher et al.

It is certified that error appears in the above-identified patent and that said Letters Patent is hereby corrected as shown below:

In the Specification

Column 1, Line 62 - DELETE "Maser" and INSERT -- laser --.

Signed and Sealed this
Seventeenth Day of April, 2018

Andrei Iancu
*Director of the United States Patent and Trademark Office*